(12) United States Patent
Knox

(10) Patent No.: US 6,332,887 B1
(45) Date of Patent: Dec. 25, 2001

(54) SPINAL FUSION INSTRUMENTATION SYSTEM

(76) Inventor: Benjamin D. Knox, 4895 Judith's Garden Rd., Oxford, MD (US) 21654

( * ) Notice: Subject to any disclaimer, the term of this patent is extended or adjusted under 35 U.S.C. 154(b) by 0 days.

(21) Appl. No.: 09/348,870

(22) Filed: Jul. 7, 1999

Related U.S. Application Data

(60) Provisional application No. 60/127,950, filed on Apr. 6, 1999.

(51) Int. Cl.$^7$ ................................................ A61B 17/15
(52) U.S. Cl. .................. 606/87; 606/61; 606/69; 606/80; 606/96; 606/105
(58) Field of Search ................... 606/60, 61, 72, 606/73, 79, 80, 86, 87, 88, 96, 102, 104, 105, 201, 210, 215, 217, 219, 235

(56) References Cited

U.S. PATENT DOCUMENTS

| | | | |
|---|---|---|---|
| 4,718,413 | * 1/1988 | Johnson | 606/82 |
| 4,907,577 | 3/1990 | Wu | 606/87 |
| 5,246,458 | 9/1993 | Graham | 606/60 |
| 5,344,423 | 9/1994 | Dietz et al. | 606/87 |
| 5,415,663 | 5/1995 | Luckman et al. | 606/86 |
| 5,423,826 | 6/1995 | Coates et al. | 606/96 |
| 5,425,772 | 6/1995 | Brantigan | 623/17 |
| 5,445,639 | 8/1995 | Kuslich et al. | 606/80 |
| 5,489,307 | 2/1996 | Kuslich et al. | 623/17 |
| 5,645,549 | 7/1997 | Boyd et al. | 606/96 |
| 5,653,714 | 8/1997 | Dietz et al. | 606/87 |
| 5,700,291 | 12/1997 | Kuslich et al. | 623/17 |
| 5,735,856 | 4/1998 | McCue et al. | 606/87 |
| 5,741,253 | 4/1998 | Michelson | 606/61 |
| 5,785,707 | 7/1998 | Boyd et al. | 606/41 |
| 5,865,846 | 2/1999 | Bryan et al. | 623/17 |
| 6,063,088 | * 5/2000 | Winslow | 606/61 |

OTHER PUBLICATIONS

Internet web page An abbreviated version of "Acquired SpinePathology" by Ken Randall, as adapted by Vince Lepak, Apr. 1, 1998; Univ Of Oklahoma, Dept. Of Physical Therapy Theory & Methods II; Internet http://w3.ouhsc.edu/llepak/courses/3233/98/course/spinesurg. html.

* cited by examiner

Primary Examiner—David O. Reip
(74) Attorney, Agent, or Firm—Heller Ehrman White & McAuliffe LLP

(57) ABSTRACT

Instrument systems and methods for the fusion of two or more adjacent vertebrae include devices to facilitate placement of screws and plates to stabilize the vertebrae and instruments to facilitate parallel decortication of the vertebral endplates prior to insertion of the bone graft. A targeter allows proper placement of a plurality of vertebral screws into the vertebral bodies. A distractor is temporarily attached to the vertebral screws and a bushing is inserted between the two arms of the distractor. The bushing acts as a guide for a cutting tool, to allow the perfect parallel decortication of the vertebral endplates. After insertion of the bone graft, a plate is affixed to the vertebral screws using locking screws, to stabilize the joint so that fusion may occur. The invention features a novel bushing that allows parallel decortication of the vertebral endplates to facilitate fusion.

19 Claims, 8 Drawing Sheets

SPINAL FUSION INSTRUMENTATION SYSTEM

CROSS REFERENCE TO RELATED APPLICATIONS

This application is a continuation of and claims priority to U.S. Provisional Patent Application Ser. No. 60/127,950, entitled "Spinal Instrumentation," filed Apr. 6, 1999.

BACKGROUND OF THE INVENTION

1. Field of the Invention

The invention relates to methods and apparatus useful for the fusion of two or more adjacent vertebrae. The present invention incorporates novel devices to facilitate placement of screws and plates to stabilize the vertebrae, and a novel system for the parallel decortication of the vertebral endplates prior to insertion of the bone graft.

2. Description of the Background

Spinal fusion is commonly used in the treatment of a number of disorders of the spinal column, both in man and animals. Spinal fusion may be used to immobilize motion segments in the spine that are diseased or require stabilization due to a number of conditions, such as trauma, spinal stenosis, disc herniation, infection, tumors, spondylolisthesis, post-laminectomy and others.

During the vertebral fusion procedure, the intervertebral disc is removed and a bone graft or other graft material is placed between the contiguous vertebrae, which may then be stabilized using a suitable implant, such as a plate. To maximize the formation of a strong callus between the fused vertebrae, the endplates of the two vertebrae are decorticated prior to insertion of the graft. Decortication is a tedious but important part of the surgical procedure. Due to the close proximity of the spinal cord and other fragile structures to the surgical site, a reliable system is needed to prepare the vertebrae for fusion, including decortication of the vertebrae and preparation of the vertebrae for the installation of the fixation plate.

There are a number of methods and devices that have been used to facilitate stabilization or repair of damage to the spinal column. There are also a number of devices which are useful to prepare the bones of the spinal column and other joints to receive implants or fixation devices. For example, artificial discs have been used to replace damaged human intervertebral discs. In one such procedure, a router guide is first used to cut elongate channels into the bodies of the two adjacent vertebrae to receive the cylindrical shaped members of the implant. In this procedure, an artificial disc is used to replace the damaged intervertebral disc, as opposed to a fusion procedure in which the disc is removed and the vertebrae are fused to each other. (U.S. Pat. No. 5,246,458). In another procedure using a disc endoprosthesis, concave surfaces are cut in the inferior and superior surfaces of the opposing vertebral bodies using a bone surface milling jig (jig not shown), prior to implantation of the endoprosthesis. (U.S. Pat. No. 5,865,846). In still another procedure using a spinal fusion implant, two cylindrical cavities are reamed immediately next to one another within the disc space. A cylindrical reamer is passed through a tubular guide laparoscopically. (U.S. Pat. No. 5,489,307 and U.S. Pat. No. 5,700,291).

In addition to methods using artificial implants in the intervetebral spaces, other devices have been developed to facilitate surgical manipulation of the vertebrae. For example, a drill and tap guide system has been used to make screw holes in vertebrae to be instrumented (U.S. Pat. No. 5,423,826). Template assemblies have been used to mark locations on the disc annulus for implantation of an interbody fusion device or introducing a working instrument (U.S. Pat. No. 5,645,549 and U.S. Pat. No. 5,785,707). In addition, a spinal transpedicle drill jig has been used to provide a safe route for drilling screw holes through the pedicles of the vertebrae (U.S. Pat. No. 4,907,577). However, none of these devices is suitable for nor provides a method or apparatus for the parallel decortication of the vertebral endplates prior to spinal fusion with a bone implant (or other bone-like implant capable of promoting fusion), and more specifically, one in which means are provided to prevent damage to the spinal cord.

With respect to other areas of the body, a number of devices have been developed to facilitate the removal of bone before implantation of a fixation device or other surgical manipulation. One such procedure utilizes an orthopedic cutting guide and bushing having a bore therethrough to prepare a femur for knee revision surgery (U.S. Pat. No. 5,735,856).

In another procedure involving the femur, a dual slide cutting guide which accommodates a milling burr is used in milling planar surfaces on a femur (U.S. Pat. No. 5,653,714). With respect to preparation of the tibia, a template may be used to mill planar surfaces on the articular surface of the tibia. A pivot arm is used to guide the depth of the cutting burr, thereby creating a planar cut in the bone surface (U.S. Pat. No. 5,344,423).

Another device for preparing the knee incorporates a saw guide, including a constrained slot for guiding the saw, useful for making cuts in the bones of the knee joint during prosthesis implantation surgery (U.S. Pat. No. 5,415,663). The foregoing devices, although quite useful in preparing the long bones of the legs, are not suitable for use on the vertebral column, and more particularly, for use in the decortication of the vertebral endplates.

SUMMARY OF THE INVENTION

The invention overcomes the problems and disadvantages associated with current strategies and designs, and provides a novel system to facilitate decortication of the vertebral endplates and the fusion of adjacent vertebrae. The system employs a targeter which allows proper placement of a plurality of vertebral screws in the vertebral bodies. A distractor is then temporarily attached to the vertebral screws, and the disc space is distracted. A bushing is then inserted between the two arms of the distractor. The bushing acts as a router guide for a cutting bit, to allow the perfect parallel decortication of the vertebral endplates. At this juncture, surgical decompression of the spinal nerve roots or the spinal cord may be undertaken if indicated, using conventional methods. After insertion of a bone graft, a plate is affixed to the vertebral screws using locking screws, further stabilizing the joint so that fusion may occur.

One embodiment of the invention is directed to a spinal fusion instrument system or assembly comprising a bushing, which defines an opening, and means for mounting the bushing on two contiguous vertebrae. The opening in the bushing is configured to guide a cutting tool to allow parallel decortication of the opposing endplates of the two contiguous vertebrae. Preferably, the opening defined by the bushing has two parallel sides which are disposed parallel to the opposing endplates when the bushing is mounted on the contiguous vertebrae.

Another embodiment is directed to an apparatus for guiding a cutting tool to prepare two contiguous vertebrae for fusion to each other comprising a bushing, which defines a first hole therethrough, and a mounting member for mounting the bushing on the two contiguous vertebrae. The hole of the bushing is configured to guide the cutting tool during decortication of opposing endplates of the two contiguous vertebrae.

Another embodiment is directed to an apparatus for guiding a cutting tool to prepare two contiguous vertebrae for fusion to each other comprising a bushing, which defines a first hole therethrough, and a means for mounting the bushing on the two contiguous vertebrae. The hole of the bushing is configured to guide the cutting tool during decortication of opposing endplates of the two contiguous vertebrae.

Another embodiment is directed to a method for preparing two vertebrae for spinal fusion comprising placing a first vertebral screw and a second vertebral screw into the anterior aspect of a first vertebral body, placing a third vertebral screw and a fourth vertebral screw into the anterior aspect of a second vertebral body, the first and the second vertebral bodies being contiguous to each other, mounting a distractor on the first, second, third and fourth vertebral screws, the distractor comprising two distractor arms, distracting the disc space between the two vertebrae, mounting a bushing between the two distractor arms, the bushing defining a first guide hole therethrough, inserting a cutting tool through the guide hole to cut away the target tissue, and removing the target tissue. The method may also comprise the step of surgically decompressing the spinal nerve roots or spinal cord, if indicated, using conventional means.

Another embodiment is directed to a method for fusing two contiguous vertebrae to each other comprising placing a first vertebral screw and a second vertebral screw into an anterior aspect of a first vertebral body, placing a third vertebral screw and a fourth vertebral screw into an anterior aspect of a second vertebral body, the first and the second vertebral bodies being contiguous to each other, mounting a distractor on the first, second, third and fourth vertebral screws, the distractor comprising two distractor arms, distracting the disc space between the two vertebrae, mounting a bushing between the two distractor arms, the bushing defining a first guide hole therethrough, inserting a cutting tool through the guide hole to cut away the target tissue, removing the target tissue, placing a bone graft between the first and second vertebral bodies, and allowing the two contiguous vertebrae to fuse. In a preferred embodiment, the method further comprises the step of stabilizing the first and second vertebral bodies and bone graft with a fixation plate. The method may also comprise the step of surgically decompressing the spinal nerve roots or spinal cord, if indicated.

Another embodiment is directed to a method for guiding a cutting tool during removal of a target portion of a bone comprising the steps of mounting a bushing on the bone, the bushing defining an opening therethrough which is sized to restrict passage of a collar on the cutting tool, inserting the cutting tool through the opening, and cutting away the target portion.

Other objects and advantages of the invention are set forth in part in the description which follows, and in part, will be obvious from this description, or may be learned from the practice of the invention.

DESCRIPTION OF THE DRAWINGS

FIG. 5D Top view of the distractor of FIG. 5B.

FIG. 6B Top view showing a cross section of a distractor arm and an engagement portion of a bushing having an arcuate engagement portion.

FIG. 6C Top view showing a cross section of a distractor arm and an engagement portion of a bushing having a square engagement portion.

FIG. 6D Top view showing a cross section of a distractor arm and an engagement portion of a bushing having an I-shaped engagement portion.

FIG. 6E Side view showing a bushing being engaged with the distractor.

DESCRIPTION OF THE INVENTION

As embodied and broadly described herein, the present invention is directed to a novel system and method for the fusion of vertebrae. The system employs a targeter which allows proper placement of a plurality of vertebral screws in the vertebral bodies. A distractor is then temporarily attached to the vertebral screws and a novel bushing is inserted between the two arms of the distractor. In a preferred embodiment, the bushing acts as a router guide for a cutting bit, to allow precise parallel decortication of the vertebral endplates. After insertion of the bone graft, a plate is affixed to the vertebral screws using locking screws to stabilize the joint, so that fusion may occur. The invention features a novel bushing that allows parallel decortication of the vertebral endplates to facilitate fusion.

Targeter

Figure 1:
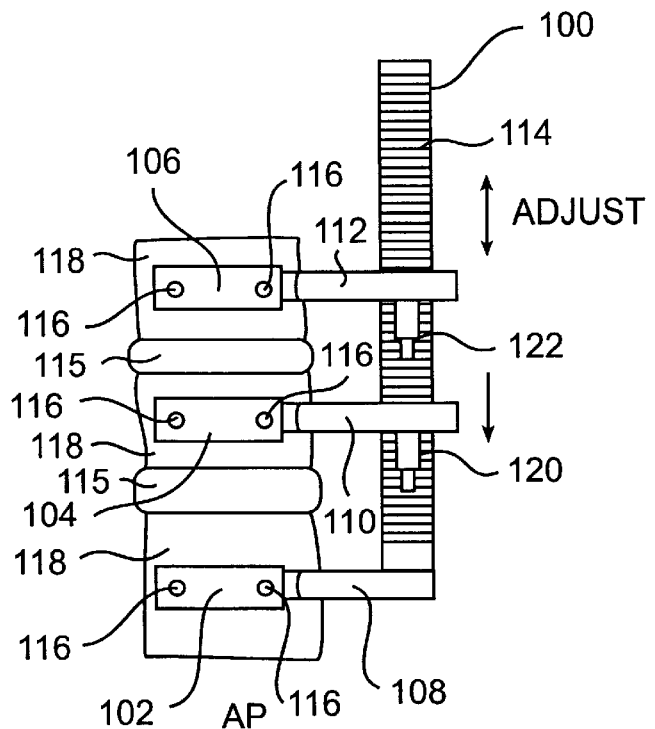
FIG. 1 Anteroposterior view of a targeter according to the present invention and three adjacent vertebrae.
Figure 2:
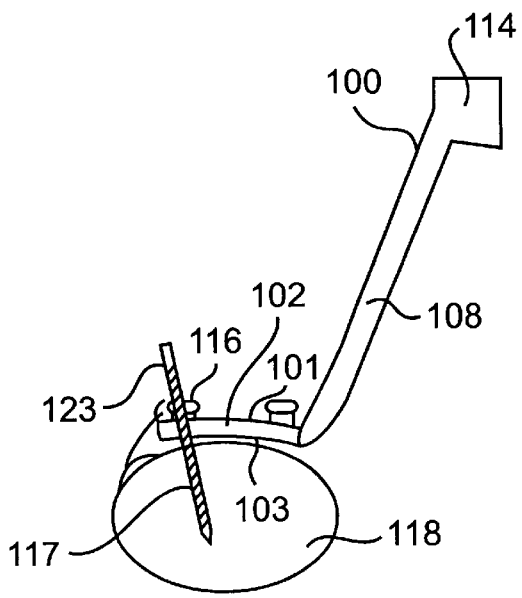
FIG. 2 Transverse view of the targeter being used to guide a drill bit into a vertebra.
Figure 5A:
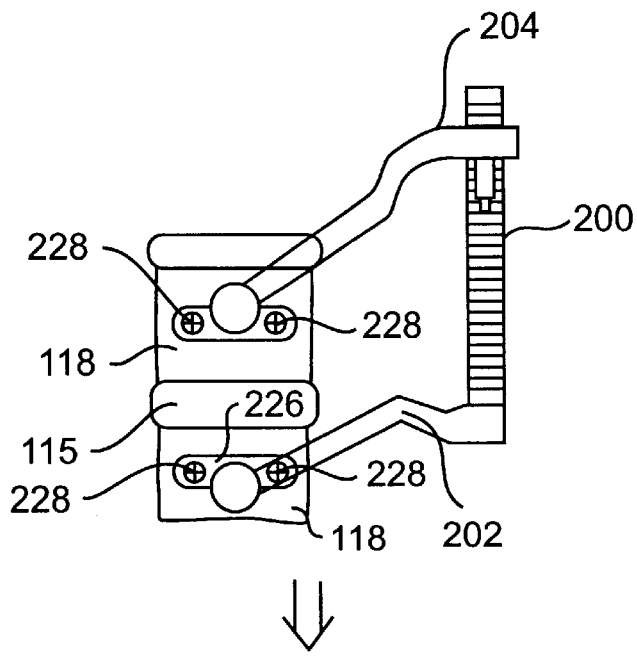
FIG. 5A Anteroposterior view of a distractor engaged with two vertebrae according to the present invention.
Figure 5B:
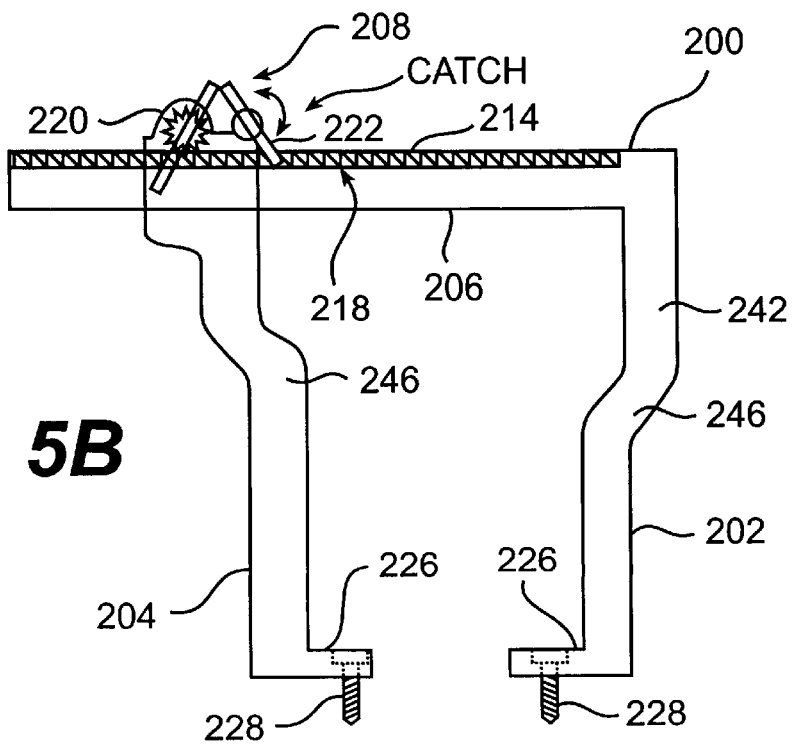
FIG. 5B Side view of a distractor showing a rack and pinion mechanism.
Figure 5C:
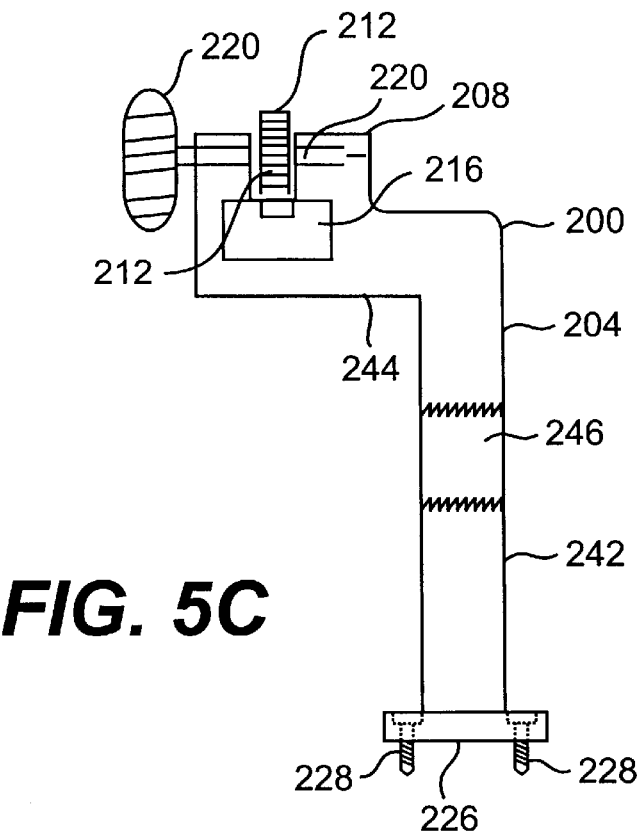
FIG. 5C End view of the distractor of FIG. 5B.
Figure 5D:
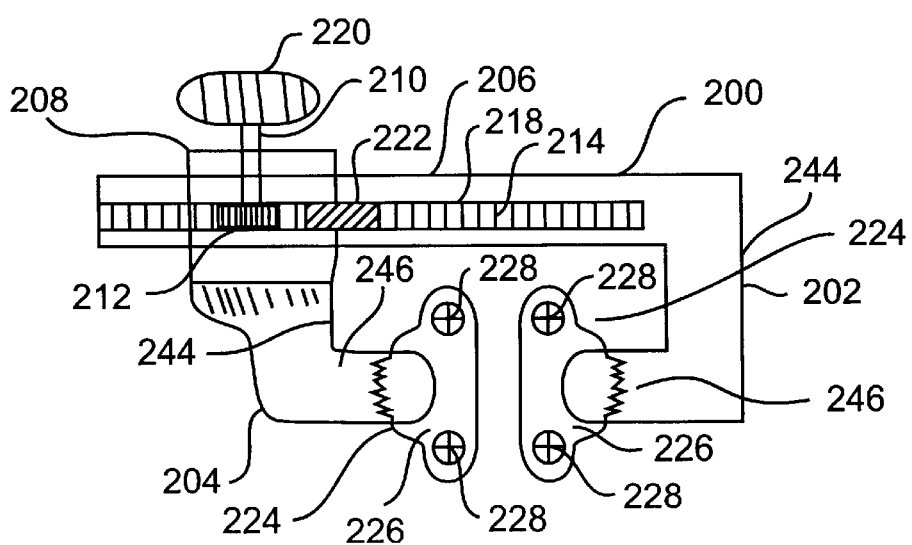

The first component of the system is the targeter, which is used to facilitate placement of vertebral screws into the anterior aspect of two contiguous vertebrae. A preferred embodiment of the targeter is depicted in FIGS. 1–2. In all the Figures, like reference numerals refer to like elements, so that a further description thereof is omitted. Referring to FIGS. 1–2, targeter 100 comprises a series of two or more drill guide portions 102, 104, and 106. Each drill guide portion has an anterior face 101 and a posterior face 103 and a plurality of drill guide holes 116 therethrough. In a preferred embodiment, anterior and posterior faces 101 and 103 are rectangular in anteroposterior projections and slightly curved transversely so that they approximate the contours of the vertebral bodies. Two drill guide holes 116 are placed through each guide portion along the central longitudinal axes of the faces. The two guide holes on each guide portion are spaced apart so that they match the spacing of the holes 502 in the plate 500 which will ultimately be affixed (FIG. 9), as well as the spacing of the holes in the face plates 226 of the distractor 200 (FIG. 5D).

Each drill guide portion 102, 104, and 106 is preferably connected by individual arms 108, 110, and 112 to rail 114. As discussed below, the spacing between the drill guide portions 102, 104 and 106 along rail 114 may be adjusted, to allow the appropriate placement of drill holes 117 through drill guide holes 116 of the drill guide portions into the anterior vertebral cortex and into the marrow of vertebral bodies 118.

Although all arms may be movable, one arm 108 is preferably affixed to rail 114, while the other arms 110 and 112 are adjustable, and are connected to rail 114 by an adjustment mechanism. A preferred adjustment mechanism 120 comprises a rack and pinion mechanism 122. Specifically, the adjustable arms 110 and 112 ride on rail 114 in rack and pinion fashion. As will be clear to those of skill in the art, other types of adjustment mechanisms may be used to alter the spacing between the guide portions.

Targeter 100 is constructed so that the drill guide portions may be placed inside the wound. During use, drill guide portions 102, 104 and 106 are placed inside the wound, while adjustment mechanism 120 and rail 114 lie outside the wound.

As will be clear to those of skill in the art, only two drill guide portions, i.e., fixed guide portion 102 and movable guide portion 104, would be needed perform a single level fusion. In contrast, one fixed and two movable guides could be placed on the rail to perform a two level fusion. Additional guide portions may be added as needed for multiple level fusions.

Targeter 100 is designed so that the drill holes 117 placed in the vertebral bodies 118 will align with the appropriate holes in the plate that will be ultimately inserted. In operation, targeter 100 is held in the desired position, with both of the two drill guide holes 116 on one of the guide portions (i.e., guide portion 102 or 104) centered in the middle (midway between the discs 115) of the vertebral body 118 that is to be drilled first; each drill guide hole 116 is preferably placed equidistant from the midline of the vertebral body. Any hole may be drilled first, and the first drill bit 123 is left in place. Slight rotation of the entire targeter 100 about the first drill bit 123 can then be performed to fine tune the positioning of the guide portions of the targeter. The spacing of the guide portions can be adjusted if necessary. A second hole is then drilled with a second drill bit, preferably in the other vertebral body. The first drill bit 123 and second drill bit may be left in place to facilitate proper placement of the positions of the remaining guide holes 116. The remaining drill holes 117 can be drilled, and all drill bits and targeter 100 removed.

Figure 3:
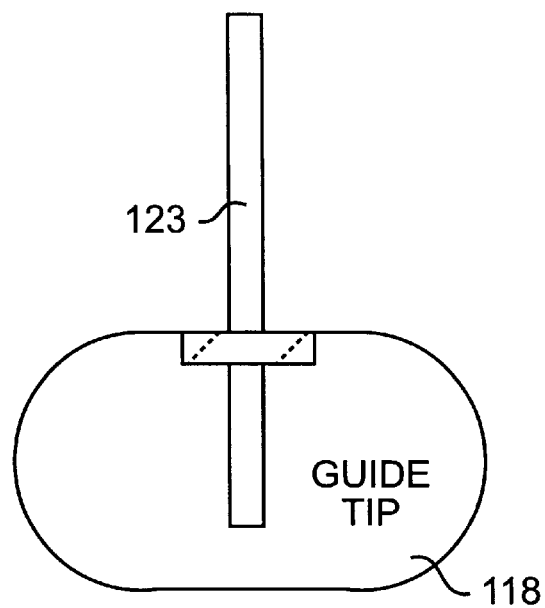
FIG. 3 Transverse view of a vertebra being prepared to receive vertebral screws.
Figure 4:
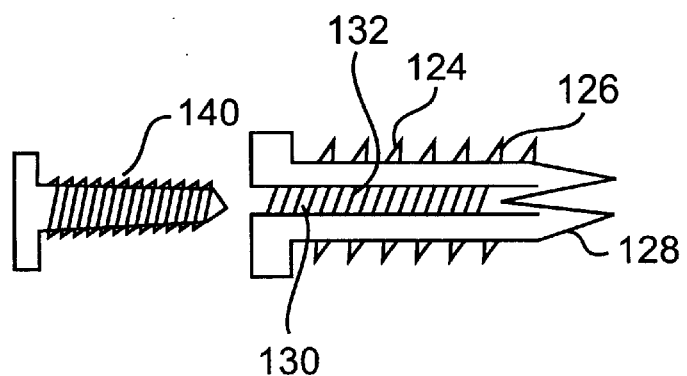
FIG. 4 Cross-sectional view of a locking screw and a cross-sectional cutaway view of a vertebral screw with an expandable tip according to the present invention.

Referring to FIGS. 3–4, the drill holes 117 are then countersunk to allow the vertebral screw head to sit flush with the surface of the vertebra, and tapped using a suitable tapping device. Vertebral screws 124 are inserted into each hole. In a preferred embodiment, vertebral screws 124 are hollow, and have an outer thread 126 which engages the cancellous bone of the vertebra, an expandable tip 128, and an inner thread 130 around cavity 132, which is adapted to receive both the distractor screws 228 of distractor 200 as well as locking screws 140 used to affix the plate to the vertebrae.

Distractor

The next component of the system is the distractor. The distractor distracts the disc space, and also serves as a base for mounting the bushings of the present invention, which are used to guide the cutting tool during decortication of the vertebral endplates.

A preferred embodiment of the distractor is depicted in FIGS. 5A–5D. Distractor 200 comprises a fixed arm 202 and an adjustable arm 204 attached to a rail or bar 206. Adjustable arm 204 is preferably attached to bar 206 via an adjustment mechanism 208. Although any suitable adjustment mechanism may be used, in a preferred embodiment, a rack and pinion mechanism, that remains outside the wound, is used. In this embodiment, rack and pinion mechanism comprises a pinion 210 having gears 212, which engage teeth 214 within channel 216 of rack 218 on bar 206. Thumbscrew 220 is turned manually to turn pinion 210, and catch 222, which may be spring loaded, engages teeth 214 and prevents loss of distraction. The rack and pinion mechanism applies a distracting force between the fixed and movable arm of the distractor.

Arms 202 and 204 of the distractor each comprise a long portion 242 and a short portion 244 which are preferably disposed at right angles to each other. The long portion 242 is preferably designed with a slight crook 246, or a "bayonet" configuration, which lies in a plane perpendicular to short portion 244. As can best be seen in FIGS. 5B and 5D, the short portions 244 and crooks 246 of fixed arm 202 and movable arm 204 and their attachment mechanisms 224 are preferably configured so that they are mirror images of each other. Crooks 246 allow for a bushing to be freely inserted between opposing arms 202 and 204 without interference with the short portions 244 of each arm. The end of short portion 244 of fixed arm 202 (opposite the end attached to long portion 242) is fixedly attached to bar 206. The end of short portion 244 of adjustable arm 204 (opposite the end attached to long portion 242) is coupled to bar 206 via adjustment mechanism 208.

An attachment mechanism 224 is attached to long portion 242 of each distractor arm at the end of long portion 242 opposite the end which is attached to short portion 244. Attachment mechanism 224 comprises a face plate 226 and two distractor screws 228. Distractor screws 228 are used to temporarily secure face plate 226 to each vertebral body 118 via the inner threads 130 of the vertebral screws 124, which have previously been placed in the vertebrae.

The distractor screws 228 are preferably positioned so that they are offset relative to the point where long portion 242 of distractor arm (202 or 204) joins face plate 226. In other words, screws 228 are positioned on face plate 226 at an end opposite the end where the distractor arm joins the face plate (FIG. 5B). This offset feature provides room for the bushing between the distractor arms and provides easier access to the opening in the bushing for the cutting tool. Without this offset (i.e., if the long portion of the arm was disposed directly between the attachment screws) there would be very little space upon which the collet of the cutting tool could rest and be stabilized.

In operation, the arms of the distractor are placed so that they are appropriately spaced, and the attachment mechanism 224 on each arm is connected to the vertebral screws 124 using distractor screws 228. The distractor screws 228 are long enough to engage the inner threads 130 of the vertebral screws 124, but are not long enough to deploy the expandable tips 128 of the vertebral screws 124. The disc space is then distracted and any discectomy or decompression (i.e., of spinal nerve roots or spinal cord) is performed.

Note that the arms 202 and 204 and face plates 226 are configured so that when the distractor is connected, the arms 202 and 204 are farther away from the disc space than the vertebral screws 124.

Bushings

After the distractor has been fixed in place, a bushing is inserted between the arms to guide the cutting instrument used to prepare the intervertebral region for fusion. A preferred bushing useful in the present invention is depicted in FIG. 6A.

Figure 6A:
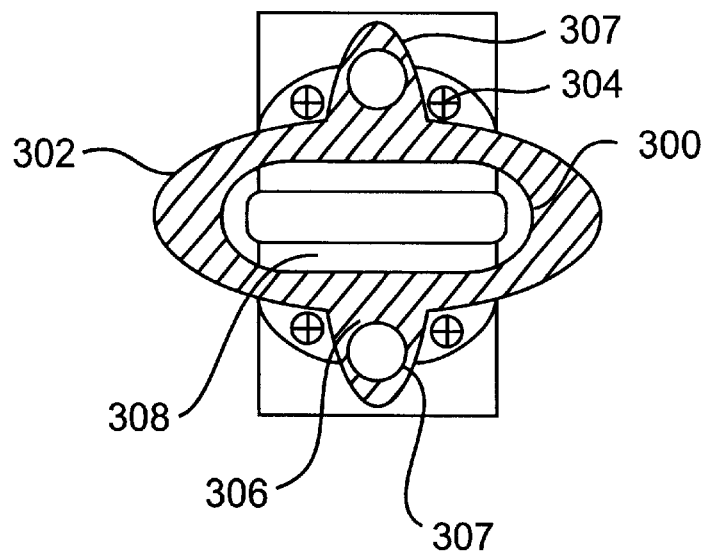
FIG. 6A Anteroposterior view of a bushing according to the present invention.

As depicted in FIG. 6A, bushing 300 comprises a body 302, two engagement portions 304 and 306, and a guide hole 308. Guide hole 308 is preferably rectangular in shape (with or without rounded corners). The opposite sides of guide hole 308 along its length are parallel to each other. Engagement portions 304 and 306 each have a cavity or notch 307 for mating engagement or interdigitation with the distractor arms.

Figure 7:
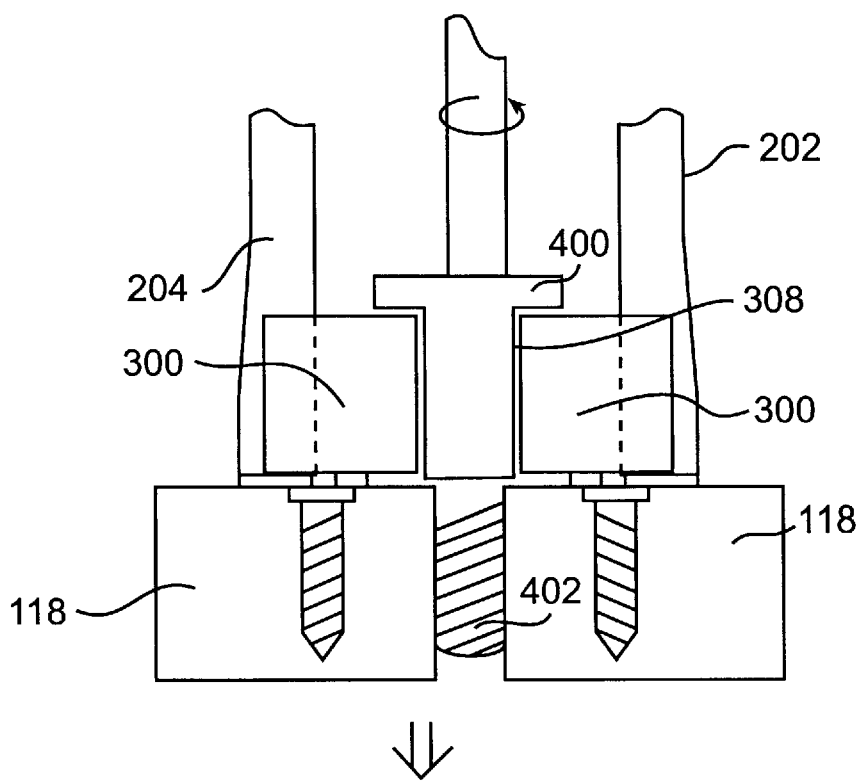
FIG. 7 Sagittal cross-sectional view of a bushing, distractor and a cutting tool engaged with the bushing.

The bushing may be made in a variety of desired sizes to accommodate different patient sizes and post-distraction spacing distances. As best shown in FIG. 7, bushing 300 is configured to essentially act as a "router guide" for perfect parallel decortication of the vertebral endplates.

Figure 6B:
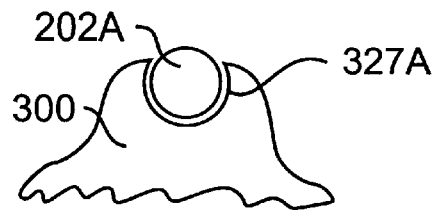
Figure 6C:
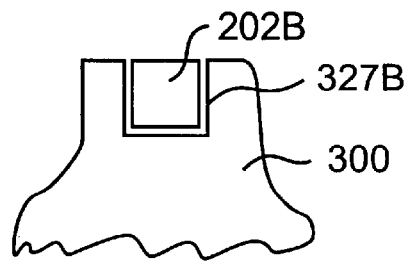
Figure 6D:
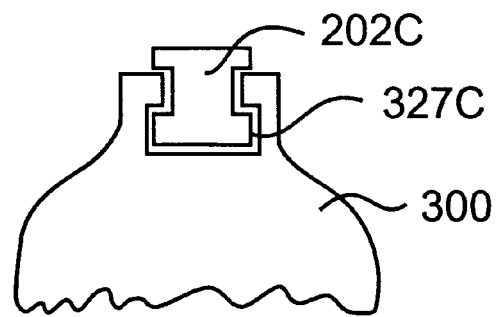

When bushing 300 is inserted between the two arms 202 and 204 of the distractor 200, cavities 307 of engagement portions 304 and 306 engage arms 202 and 204. FIGS. 6B, 6C and 6D, depict some useful configurations of the engagement portions of the bushing and the distractor arms. For example, in FIG. 6B, arcuate cavity 327A engages with rounded distractor arm 202A. In FIG. 6B, square cavity 327B engages with rectangular or square distractor arm 202B. In FIG. 6C, T-shaped cavity 327C engages with I-shaped arm 202C. As will be clear to those of skill in the art, other configurations are possible, and may be substituted in place of the examples shown.

Figure 6E:
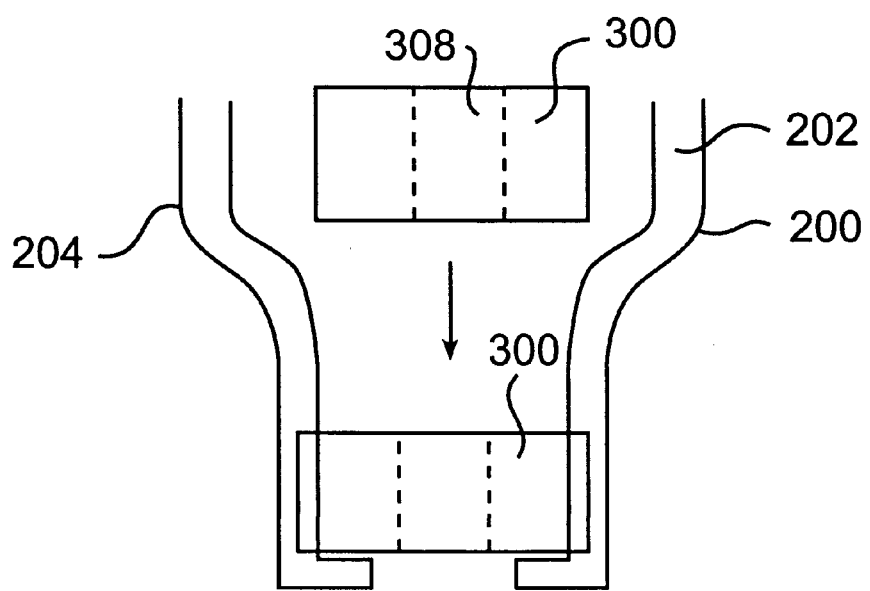

The engagement configurations depicted in FIGS. 6B-D allow for the interdigitation of the bushing and the distractor arms. These geometries allow "drop in" insertion of the bushing parallel to the long portions 242 of the distractor arms down to the intervertebral disc space As depicted in FIG. 6E, the bushing slides easily between the two parallel arms.

The embodiment of FIG. 6A is particularly adapted for use with a router bit. Referring to FIG. 7, collar 400 prevents router bit 402 from penetrating too deeply. In a preferred embodiment, collar 400 prevents bit 402 from penetrating any deeper than 14 mm. As a result, the posterior-most aspect of the two endplates of the vertebrae may be left intact, and the bit is prevented from any possible contact with the spinal cord. Modular collars may be utilized to allow for deeper or more superficial penetration where appropriate.

Current cervical plating systems require that decortication and fusion techniques be performed freehand, independently of the plating system. In contrast, using the novel system of the present invention, the decortication becomes a more accurate, "machined" process and is integrated into the instrumentation itself.

Figure 8:
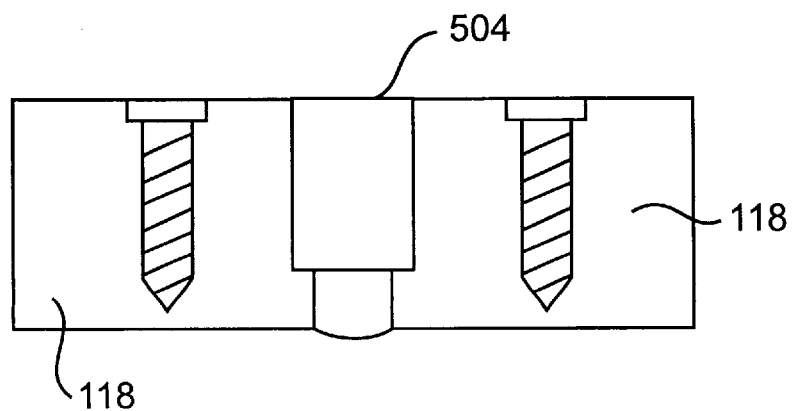
FIG. 8 Sagittal cross-sectional view showing two adjacent vertebrae which have been prepared for fixation.

After bushing 300 is in place, a high-speed bone cutting bit (the "decorticator") of the desired diameter, such as router bit 402, is inserted through and is guided by the bushing. The endplates of the vertebrae adjoining the disc space are decorticated, creating an ideal receptacle for the bone graft 504 (FIG. 8) which has decorticated bone surfaces that are flat and parallel to one another.

Figure 10:
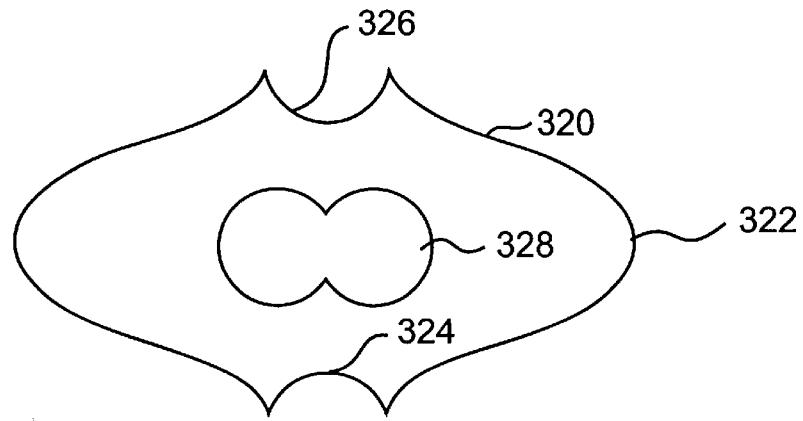
FIG. 10 Another embodiment of a bushing according to the invention.

Another embodiment of a bushing according to the present invention is depicted in FIG. 10. FIG. 10 is an embodiment of a bushing having a guide hole 328 in the shape of two overlapping holes. Bushing 320 comprises a body 322, two engagement portions 324 and 326 and guide hole 328. Guide hole 322 has the shape of two overlapping round holes. This configuration is ideally suited for use with a drill. For example, a stop drill may be used with this bushing to prepare the vertebrae for an implant or graft. The intervertebral space after preparation by this technique has the shape of two partially overlapping cylinders and is preferably grafted by prefabricated bone or a bone substitute of the same shape.

Figure 11:
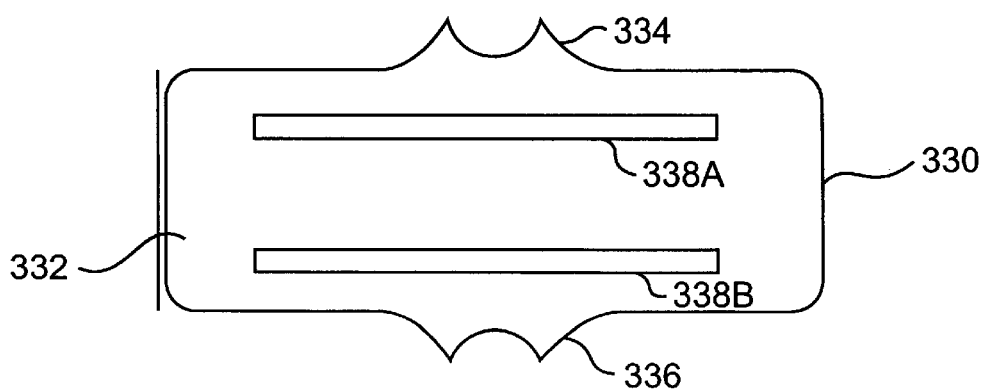
FIG. 11 Another embodiment of a bushing according to the invention.

FIG. 11 depicts still another embodiment of a novel bushing according to the present invention. Bushing 330 comprises a body 332, two engagement portions 334 and 336 and two parallel slits 338A and 338B. These slits are particularly useful to guide an oscillating saw to prepare the vertebrae for a bone graft. The intervertebral space after preparation by this technique has the same shape as the "router" technique, i.e., parallel decorticated endplates.

Graft insertion, and fixation with a plate

After the implantation site has been prepared, bone graft is harvested from the iliac crest or other suitable source using an oscillating saw with dual parallel blades, creating a piece of the exact thickness necessary to span the decorticated disc space. Alternately, a suitable bone graft substitute could be used. The anteroposterior and left to right dimensions of the bone graft may be adjusted with manual instruments (rongeurs), and the bone graft impacted into place. The distractor is removed. For two level fusions, the distractor is repositioned and the process repeated.

Figure 9:
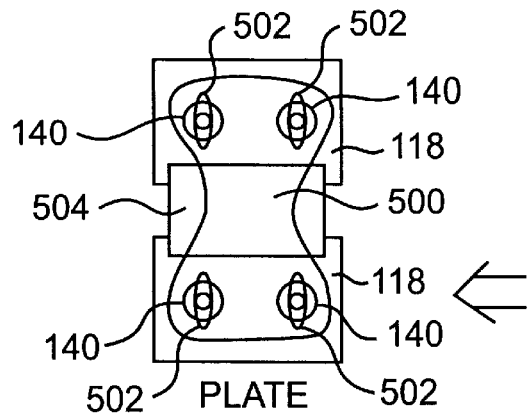
FIG. 9 Anteroposterior view of two vertebrae following preparation, decortication and bone graft implantation, with a fixation plate in place.

Finally, as shown in FIG. 9, after implantation of graft 504, a plate of the appropriate size, such as fixation plate 500 is selected, and secured with locking screws 140, which are inserted through holes 502 in plate 500. As shown in FIG. 4, locking screws are configured for mating engagement with cavity 132 of the vertebral screws. As locking screws 140 are tightened, the expandable tips 128 of the vertebral screws 124 are deployed.

As will be clear to those of skill in the art, a range of plate sizes can be made so that any spacing obtained or desired may be accommodated. Holes 502 in plates 500 are preferably elliptical to accommodate minor variations in spacing of the vertebral screws.

As can be seen from the foregoing, by using the various components of the present invention, spinal fusion procedures can be greatly facilitated and damage to the spinal cord avoided. Accordingly, one embodiment of the invention is directed to a spinal fusion instrument system or assembly comprising a bushing, which defines an opening, and means for mounting the bushing on two contiguous vertebrae. The opening in the bushing is configured to guide a cutting tool to allow parallel decortication of the opposing endplates of the two contiguous vertebrae. Preferably, the opening defined by the bushing has two parallel sides which are disposed parallel to the opposing endplates when the bushing is mounted on the contiguous vertebrae.

The means for mounting may comprise any suitable mechanism. In a preferred embodiment, the means for mounting comprises a plurality of vertebral screws placed in the two contiguous vertebrae and a distractor having two distractor arms adapted for engagement with the plurality of vertebral screws. In this embodiment, the bushing further comprises two engagement portions for engagement with the two distractor arms. Although variations are possible without departing from the spirit and scope of the invention, in a preferred embodiment, two vertebral screws are placed in each vertebra.

The distractor may further comprise a face plate attached to each of the two distractor arms and a plurality of distractor screws. The face plates each define a plurality of holes therethrough which are adapted for receiving the plurality of distractor screws. The distractor screws are configured to be matingly received in the cavity in the vertebral screws. In a preferred embodiment, two distractor screws are placed through two holes in each of the face plates, and are then inserted into the vertebral screws, to temporarily affix the distractor to the vertebrae.

Alternately, vertebral screws or pins of various shapes and sizes may be substituted for distractor screws 228, allowing direct temporary attachment of the distractor to the vertebrae without first inserting free standing vertebral screws. Fusion could then be undertaken without instrumentation, or using instrumentation other than the preferred embodiments described herein.

In the preferred system, a targeter, such as targeter 100, may be used guide the placement of a plurality of holes in the two contiguous vertebrae for receiving the plurality of vertebral screws.

The cutting tool may comprise a collar which surrounds, in whole or in part, a cutting element. The opening in the bushing has a width smaller than the width or diameter of the collar, to prevent the cutting element from contact with the spinal cord.

Another embodiment of the invention is directed to an apparatus for guiding a cutting tool to prepare two contiguous vertebrae for fusion to each other comprising a bushing, which defines a first hole therethrough, and a mounting member for mounting the bushing on the two contiguous vertebrae. The hole of the bushing is configured to guide the cutting tool during decortication of opposing endplates of the two contiguous vertebrae. The hole allows the tool to cut away the desired portions of the vertebrae, while preventing the cutting tool from inadvertent contact with structures, such as the spinal cord.

Another embodiment is directed to an apparatus for guiding a cutting tool to prepare two contiguous vertebrae for fusion to each other comprising a bushing, which defines a hole therethrough, and a means for mounting the bushing on the two contiguous vertebrae. The hole of the bushing is configured to guide the cutting tool during decortication of opposing endplates of the two contiguous vertebrae. Decortication may comprise parallel decortication of the opposing endplates, or alternately, it may comprise partial decortication of the opposing endplates.

There are a number of useful configurations of the bushing hole. For example, in one embodiment, the hole has a rectangular or rounded rectangular shape. In another, the hole has the shape of two overlapping circles. In still another embodiment, the bushing has two holes, which comprise two parallel slits. As will be clear to those of skill in the art, other configurations of bushing holes may also be used.

The bushing may further comprise two engagement portions. The means for mounting may comprise a distractor, the distractor comprising a bar, a first arm and a second arm disposed on the bar, means for mounting or attaching the first arm on one of the two contiguous vertebrae and means for mounting or attaching the second arm on the other of the two contiguous vertebrae. The first arm is preferably fixedly disposed on the bar and the second arm is preferably movably disposed on the bar. In this embodiment, the engagement portions of the bushings each define a notch therein adapted for engagement with the distractor arms.

The distractor arms and notches are designed to interdigitate with each other. In one embodiment, the notches are arcuate in shape and the first and the second arms have a circular-shaped cross section. In another, the notches are T-shaped and the first and the second arms have an I-shaped cross section. In another embodiment, the notches are rectangular-shaped and the first and the second arms have a rectangular-shaped cross section. As used herein, "rectangular" includes both rectangles having all sides of the same length (squares) and rectangles having one pair of sides of a first length and the other pair of sides of a second length. Accordingly, in one such embodiment, the rectangular-shaped cross section may be a square.

The first and second arms preferably each comprise a first portion and a second portion. The second portion has a first end which is connected to the first portion. The second portion is disposed perpendicular to the first portion. Preferably, the second portion also has a crook in it. The second portion of each arm has a second end which is connected to the respective means for attaching that arm to the vertebra. The first and second portions of the first arm and means for attaching the first arm to the vertebra are preferably a mirror image of the first and second portions of the second arm and means for attaching the second arm to the other vertebra.

Another embodiment of the invention is directed to a method for preparing two vertebrae for spinal fusion comprising placing a first vertebral screw and a second vertebral screw into an anterior aspect of a first vertebral body, placing a third vertebral screw and a fourth vertebral screw into an anterior aspect of a second vertebral body, the first and the second vertebral bodies being contiguous to each other, mounting a distractor on the first, second, third and fourth vertebral screws, the distractor comprising two distractor arms, distracting the disc space between the two vertebral bodies, mounting a bushing between the two distractor arms, the bushing defining a guide hole therethrough, inserting a cutting tool through the guide hole to cut away the target tissue, and removing the target tissue. If necessary, the method may further comprise the step of surgically decompressing the spinal nerve roots or spinal cord after removing the target tissue.

The target tissue comprises all or at least a portion of opposing endplates of the vertebrae. The guide hole may have a rectangular shape, a rounded rectangular shape or the shape of two overlapping circles. Alternately, the bushing may define two guide holes, which comprise parallel slits.

In this method, a targeter may be used to facilitate or guide the placement of holes in the vertebrae for receiving the vertebral screws. As such, the targeter guides the placing of the first, second, third and fourth vertebral screws. The targeter preferably comprises a first drill guide portion and a second drill guide portion. The second drill guide portion is adjustably spaced apart from the first drill guide portion. The first and second drill guide portions each define two holes therethrough to guide a drill during placement of drill holes in the first and second vertebral bodies.

As will be clear to those of skill in the art, the drill holes and the four vertebral screws may be installed in any order. However, in a preferred method, the first and third vertebral screws are placed prior to the second and fourth vertebral screws. In other words, the first two screws are placed in different vertebrae. Additional or fewer vertebral screws may be utilized as desired without departing from the spirit and scope of the invention.

The distractor is preferably mounted by inserting at least two distractor screws through a first plate affixed to an end of one of the two distractor arms and inserting at least two distractor screws through a second plate affixed to the other of the two distractor arms, and attaching the first and second plates to the vertebrae by inserting the distractor screws into the first, second, third and fourth vertebral screws. Useful cutting tools in the practice of the present invention include router bits, oscillating saws and other suitable drills, such as a stop drill.

Another embodiment is directed to a method for fusing two contiguous vertebrae to each other comprising placing a first vertebral screw and a second vertebral screw into the anterior aspect of a first vertebral body, placing a third vertebral screw and a fourth vertebral screw into the anterior aspect of a second vertebral body, the first and the second vertebral bodies being contiguous to each other, mounting a distractor on the first, second, third and fourth vertebral screws, the distractor comprising two distractor arms, distracting the disc space between the two vertebral bodies, mounting a bushing between the two distractor arms, the bushing defining a first guide hole therethrough, inserting a cutting tool through the guide hole to cut away the target tissue, removing the target tissue, placing a graft, such as a bone graft, between the first and second vertebral bodies, and allowing the two contiguous vertebrae to fuse. In a preferred embodiment, the method further comprises the step of stabilizing the first and second vertebral bodies and graft with a fixation plate. The fixation plate is preferably affixed to the vertebrae using locking screws which are inserted through holes in the plate into a cavity in the vertebral screws, thereby deploying expandable tips on the vertebral screws. If necessary, the method may further comprise the step of surgically decompressing the spinal nerve roots or spinal cord after removing the target tissue.

As will be clear to those of skill in the art, in the practice of this method, the four vertebral screws may be installed in any order. However, in a preferred method, the first and third vertebral screws are placed prior to the second and fourth vertebral screws. Additional vertebral screws and locking screws may be used as desired.

The present invention may be adapted for use on other bones. Accordingly, another embodiment is directed to a method for guiding a cutting tool during removal of a target portion of a bone comprising the steps of mounting a bushing on the bone, the bushing defining an opening therethrough which is sized to restrict passage of a collar on the cutting tool, inserting the cutting tool through the opening, and cutting away the target portion.

The methods and apparatus of the present invention are preferably used in connection with efforts to stabilize the cervical vertebrae using an anterior approach. However, as will be clear to those of skill in the art, the invention may be adapted for use in other regions of the spinal column. For example, it may be used during thoracoscopic procedures in the thoracic region of the spine and during laparoscopic procedures in the lumbar region of the spine. In addition, as will be clear to those of skill in the art, the present invention is not restricted to human use, but may be adapted for use in any suitable animal.

Other embodiments and uses of the invention will be apparent to those skilled in the art from consideration of the specification and practice of the invention disclosed herein. All references cited herein, including all U.S. and foreign patents and patent applications including U.S. provisional patent application Ser. No. 60/127,950, are specifically and entirely incorporated by reference. The specification and examples should be considered exemplary only with the true scope and spirit of the invention indicated by the following claims.

I claim:
1. A spinal fusion instrument comprising:
a bushing defining an opening therethrough, said opening configured to guide a cutting tool to allow parallel decortication of opposing endplates of two contiguous vertebrae; and
means for mounting said bushing on said two contiguous vertebrae.
2. The instrument of claim 1 wherein said opening defined by said bushing comprises two parallel sides which are disposed parallel to said opposing endplates when said bushing is mounted on said contiguous vertebrae.
3. The instrument of claim 1 wherein the cutting tool comprises a collar surrounding a cutting element and wherein said opening has a width smaller than a width of the collar to prevent said cutting element from contact with the spinal cord.
4. A spinal fusion instrument comprising:
a bushing defining an opening therethrough, said opening configured to guide a cutting tool to allow parallel decortication of opposing endplates of two contiguous vertebrae; and
means for mounting said bushing on said two contiguous vertebrae, wherein the means for mounting comprises a plurality of vertebral screws placed in said two contiguous vertebrae, a distractor having two distractor arms adapted for engagement with said plurality of vertebral screws, and wherein said bushing further comprises two engagement portions for engagement with said two distractor arms.
5. The instrument of claim 4 wherein the distractor further comprises a face plate attached to each of said two distractor arms and a plurality of distractor screws, said face plates each defining a plurality of holes therethrough for receiving said plurality of distractor screws, said distractor screws configured to be matingly received in a cavity in said vertebral screws.
6. The instrument of claim 3 further comprising a targeter to guide the placement of a plurality of holes in said two contiguous vertebrae for receiving said plurality of vertebral screws.
7. An apparatus for guiding a cutting tool to prepare two contiguous vertebrae for fusion to each other comprising:
a bushing defining a non-elliptical first hole therethrough, said hole configured to guide said cutting tool during decortication of opposing endplates of said two contiguous vertebrae; and
means for mounting said bushing on said two contiguous vertebrae.
8. The apparatus of claim 7 wherein the decortication comprises parallel decortication of the opposing endplates.
9. The apparatus of claim 7 wherein the decortication comprises partial decortication of the opposing endplates.
10. The apparatus of claim 7 wherein the first hole has a rounded rectangular shape.
11. The apparatus of claim 7 wherein the bushing further defines a second hole and said first hole and said second hole comprise two parallel slits.
12. An apparatus for guiding a cutting tool to prepare two contiguous vertebrae for fusion to each other comprising:
a bushing defining a first hole therethrough, said hole configured to guide said cutting tool during decortication of opposing endplates of said two contiguous vertebrae, wherein the first hole has a shape of two overlapping circles; and
means for mounting said bushing on said two contiguous vertebrae.

13. An apparatus for guiding a cutting tool to prepare two contiguous vertebrae for fusion to each other comprising:
- a bushing defining a first hole therethrough, said hole configured to guide said cutting tool during decortication of opposing endplates of said two contiguous vertebrae;
- means for mounting said bushing on said two contiguous vertebrae; and
- wherein the bushing further comprises two engagement portions and said means for mounting comprises a distractor, said distractor comprising a bar, a first arm and a second arm disposed on said bar, means for attaching said first arm on one of said two contiguous vertebrae and means for attaching said second arm on the other of said two contiguous vertebrae, and wherein said engagement portions each define a notch therein adapted for engagement with said distractor arms.

14. The apparatus of claim 13 wherein the first arm is fixedly disposed on said bar and said second arm is movably disposed on said bar.

15. The apparatus of claim 13 wherein the notches are arcuate in shape and said first and said second arms have a circular-shaped cross section.

16. The apparatus of claim 13 wherein the notches are T-shaped and said first and said second arms have an I-shaped cross section.

17. The apparatus of claim 13 wherein the notches are rectangular-shaped and said first and said second arms have a rectangular-shaped cross section.

18. The apparatus of claim 17 wherein the rectangular-shaped cross section is a square.

19. The apparatus of claim 13 wherein the first and second arms each comprise a first portion and a second portion, each of said second portions having a first end connected to and disposed perpendicular to said first portion, said second portions each having a crook therein, said second portion of said first arm further having a second end connected to said means for attaching said first arm, and said second portion of said second arm having a second end connected to said means for attaching said second arm.

* * * * *